US007422594B2

(12) United States Patent
Zander

(10) Patent No.: US 7,422,594 B2
(45) Date of Patent: Sep. 9, 2008

(54) DRILLING TOOL GUIDE WIRE ALIGNMENT DEVICE

(75) Inventor: Nils Zander, Eckernförde (DE)

(73) Assignee: Stryker Trauma GmbH (DE)

(*) Notice: Subject to any disclaimer, the term of this patent is extended or adjusted under 35 U.S.C. 154(b) by 191 days.

(21) Appl. No.: 10/870,299

(22) Filed: Jun. 17, 2004

(65) Prior Publication Data

US 2004/0260307 A1 Dec. 23, 2004

(30) Foreign Application Priority Data

Jun. 20, 2003 (DE) ................................ 203 09 481

(51) Int. Cl.
*A61B 17/00* (2006.01)

(52) U.S. Cl. ............................ 606/80; 606/103; 606/96

(58) Field of Classification Search .................. 606/80, 606/86, 104, 96, 103; 604/164.11, 164.12, 604/164.13, 165.01, 506, 69

See application file for complete search history.

(56) References Cited

U.S. PATENT DOCUMENTS 3,171,408 A * 3/1965 Childs et al. .................. 606/96
3,480,014 A * 11/1969 Callahan ...................... 604/506
4,932,413 A * 6/1990 Shockey et al. ............. 600/434
5,133,720 A * 7/1992 Greenberg ................... 606/96
5,324,295 A * 6/1994 Shapiro ....................... 606/86
5,385,151 A * 1/1995 Scarfone et al. ............. 600/567
5,489,284 A 2/1996 James et al.
5,601,550 A * 2/1997 Esser .......................... 606/54
5,620,456 A * 4/1997 Sauer et al. ................. 606/185
5,624,447 A 4/1997 Myers
5,817,061 A * 10/1998 Goodwin et al. ....... 604/164.03
5,895,389 A * 4/1999 Schenk et al. ................. 606/96
5,951,561 A * 9/1999 Pepper et al. ................. 606/80
6,342,057 B1 * 1/2002 Brace et al. ................... 606/96

FOREIGN PATENT DOCUMENTS

DE 298 04 268 U1 6/1998
DE 198 41 253 C1 1/2000
DE 197 09 182 C2 12/2000

* cited by examiner

*Primary Examiner*—Eduardo C. Robert
*Assistant Examiner*—James L Swiger
(74) *Attorney, Agent, or Firm*—Lerner, David, Littenberg, Krumholz & Mentlik, LLP

(57) ABSTRACT

A device for installation of a guide wire for a drilling tool in a correct positional arrangement in a bone. The device includes a tissue protection sleeve, which has at one end a laterally projecting grip or handle. A trocar is provided, which trocar can be introduced into the tissue protection sleeve from the handle end and whose other end is closed. The trocar is rotatable in the tissue protection sleeve and has a central bore hole and a plurality of eccentric axially parallel bore holes, through which a guide wire can be passed. A second handle is provided which extends approximately in the same direction of the first handle and whose one end engages the end of the trocar situated the outside of the tissue protection sleeve, so that the normally freely rotatable trocar is fixed in the direction of rotation relative to the tissue protection sleeve, when both handles are manually clamped against each other.

18 Claims, 2 Drawing Sheets

44 48 42 40 38 30 36 32 34 14 10 12 18 20 46 62 52 58 16 50 54 22 56 24

12
10
14
18
20
22
24
34
32
36
30
16
38
62
40
46
52
50
42
48
44
54
56
58

DRILLING TOOL GUIDE WIRE ALIGNMENT DEVICE

BACKGROUND OF THE INVENTION

The invention relates to an instrument for the correct positional installation of a guide wire for a drilling tool in a bone.

Initial installation of a guide wire into the point of insertion is well-known for the opening of the point of insertion of a femoral nail, for example, for proximal installation. Then the bone is opened using a drilling tool threaded over the wire. An advantage of this method resides in the fact that prior to the actual drilling using a relatively large diameter, the precise position and orientation of the guide wire and, accordingly, also the subsequent bore hole can be checked with the aid of an X-ray device.

It is also well-known to initially pass a tissue protective sleeve over the guide wire, until it is in contact with the bone, in order to avoid soft tissue injury caused by the drilling tool. It is further well-known, to close the tissue protection sleeve using a trocar, in order to improve passage through the soft tissues. Subsequently, prior to the drilling operation, the trocar is removed.

U.S. Pat. No. 5,951,561 discloses a trocar having a plurality of axially parallel bores. The trocar is rotationally engaged in the tissue protection sleeve. If, at the time of X-ray inspection, it is found, for example, that the central bore is situated offset laterally to the desired position in the trocar, a second guide wire is installed in another suitable bore hole. If the second wire is positioned at the desired location, the first wire is removed and drilling is operated over the second wire.

SUMMARY OF THE INVENTION

One aspect of the invention is to provide a device for installing a guide wire for a drilling tool in correct positional arrangement in a bone, whereby ease of manipulation and precision for placing the guide wire are improved.

In the present invention, a device having a first handle and trocar which can be introduced into a tissue protection sleeve are provided. A second handle is provided, which extends approximately in the same direction as the first handle or grip and whose end engages the trocar external to the protective sleeve, so that the trocar, which is normally freely rotatable relative to the protective sleeve, is fixed in the direction of rotation, when both handles are manually tensioned in opposition to each other.

The two handles are arranged in such a way that they can be gripped together with one hand. The connection with the trocar is such that upon clamping the two handles together the trocar is fixed in its rotational position. This may be accomplished by having the trocar handle deflect into engagement with the sleeve handle. The trocar handle may be made of an elastic material such as plastic.

Different design possibilities for affixing the trocar are conceivable. One of these according to one embodiment of the invention is achieved in that the trocar has an annular recess, into which an annular engagement segment of the second handle engages so that the annular engagement segment cants into the recess and clamps the trocar, when the grips are tensioned in opposition to each other. In a surgical procedure, the second guide wire can be introduced into another bore hole, which more closely approximates the desired position, if necessary. By virtue of the clamping fixation of the trocar in the direction of rotation, the second guide wire is prevented from assuming an incorrect orientation and not attaining the desired position due to a slight relative rotation of the trocar together with the first guide wire.

Before the surgical procedure, the desired rotational position of the trocar is adjusted. To do this, according to one embodiment of the invention, the section of the trocar, at the end facing away from the protective sleeve, has a rotary knob.

The second handle is preferably made of an elastic material so that it can be deflected towards the first handle, when both handles are clamped towards each other. Preferably, the second grip is arranged above the first handle.

In order to achieve the greatest possible spatial economy, one embodiment of the invention provides that the second handle has a longitudinal slot and a deflection, bend or offset towards the first handle, so that a segment of the first handle engages in the longitudinal slot. Obviously, the first handle can have a section, which can be deflected towards the second handle and engages approximately fittingly in the slot.

According to a further embodiment of the invention, the shaft of the trocar has a shaft with a plurality of radial flanges or bands separated longitudinally, whose external diameters are somewhat smaller than the internal diameter of the tissue protection sleeve and one part of the axial bore holes in the flanges continues between the flanges as axially parallel grooves. In this embodiment, it is not necessary that the trocar have a uniform thickness over its entire length with a plurality of bore holes. The latter are situated only in the flanges, whereas axially parallel grooves or guide channels are formed on the outer surface of the trocar shaft between the flanges. This applies at least to a part of the plurality of bore holes.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
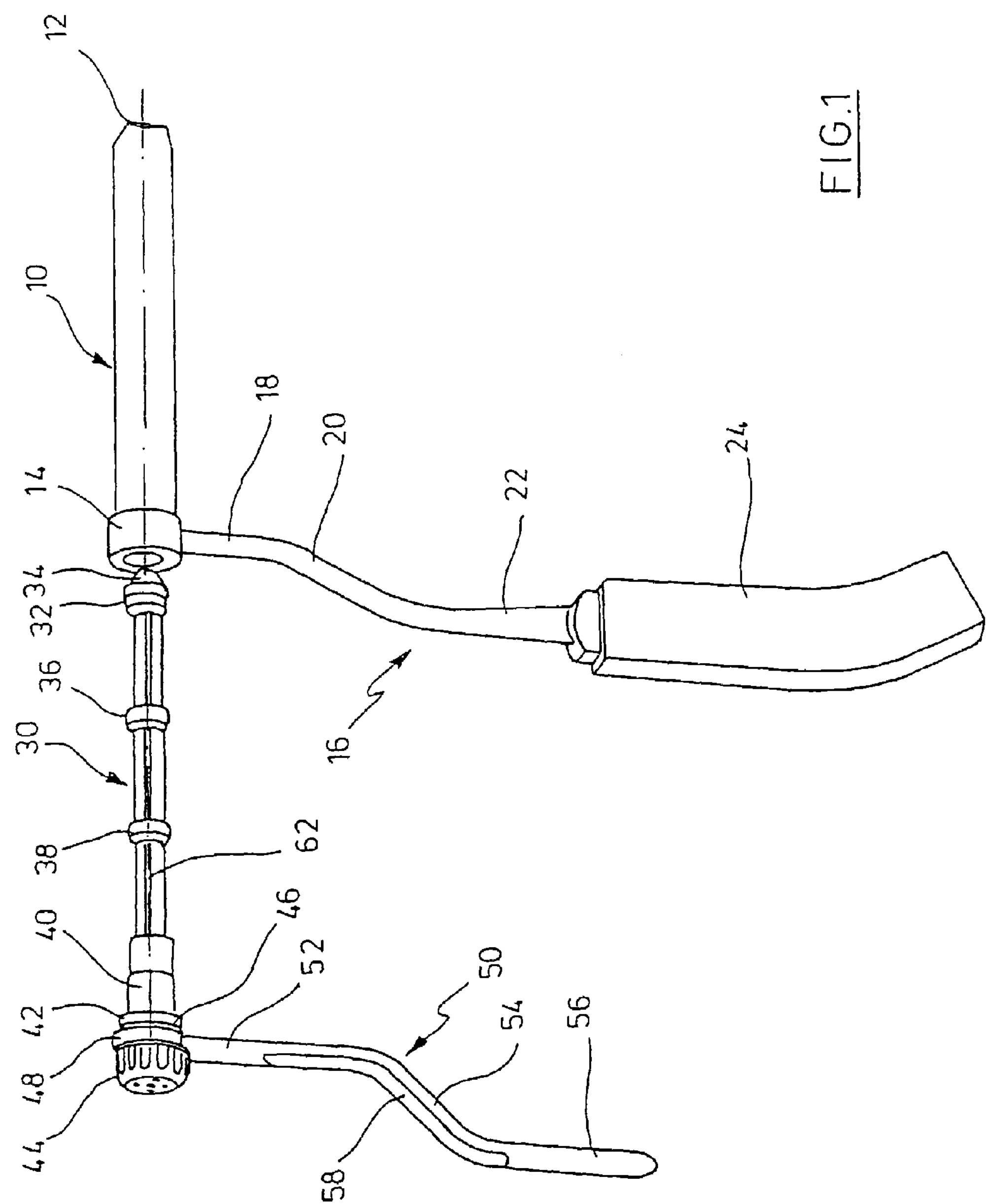
FIG. 1 is a perspective view of the device according to the invention in its disassembled condition.
Figure 2:
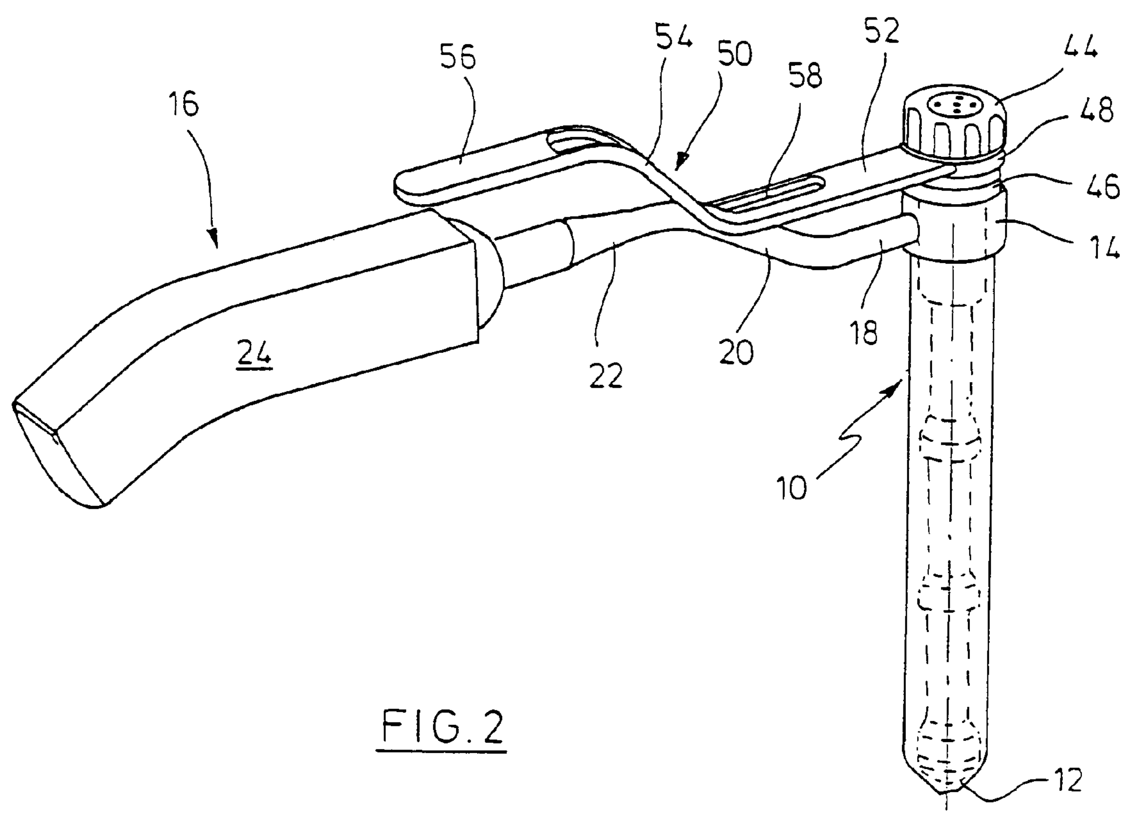
FIG. 2 is a perspective view of the device of FIG. 1 in its assembled condition.

The device represented in FIGS. 1 and 2 has a tubular tissue protection sleeve generally denoted as 10 having a distal end, which is configured as a relatively sharp irregular edge 12 and an enlarged proximal end 14, at which a radially projecting handle or grip 16 is located. The handle has a rod-like form at a first section 18 with first section 18 mounted on the enlarged end 14. A section 20 of handle 16 is deflected or bent diagonally upwards and a third section 22 is oriented approximately in the same direction as section 18. In the preferred embodiment, sections 18 to 22 are approximately circular in cross-section. A handle section 24 preferably made of plastic, for example, is coupled to section 22, whereby sections 18 to 22 can preferably be made of a metal. Handle section 24 can be pushed onto section 22.

FIG. 1 further shows a trocar generally denoted as 30, which has a stopper-shaped distal end 32 having a rounded tip 34 and a shaft extending distally from end 32. In addition, on the shaft and in axial separation two radial flanges 36, 38 are provided. In the preferred embodiment, the shaft has a smaller diameter between flanges 36, 38 and/or between the flange 36 and the stopper section 32. The external diameter of flanges 36, 38 and of section 32 is such, that it is slightly smaller than the inner diameter of tubular tissue protection sleeve 10. On the proximal end, the shaft has a terminal section 40, which also has the external diameter of the flanges 36, 38. A flange 42 having a larger diameter connects with the section 40 and a rotary knob 44 is formed at the end of the shaft. An annular recess 46 is formed between the rotary knob 44 and the flange 42. An annular section 48 of a second handle 50 is seated in the annular recess 46. The annular section 48 of handle 50 is slightly axially moveable and tiltable in the annular recess 46.

The second handle 50 has a flat first section 52, which projects approximately radially, and in the preferred embodiment, generally perpendicular to the longitudinal axis of the trocar shaft. In addition, handle 50 has a deflected or bent section 54 and a section 56 extending approximately radially forming the free end of the handle. A longitudinal slot 58 of uniform width is formed in sections 52 and 54.

At the time of assembly, the shaft of the trocar 30 is introduced into the tissue protection sleeve 10, whereby the flange 46 lies against the proximal facial edge of the end of the tissue protection sleeve 10. Handles 16 and 50 are arranged above one another and upon insertion of the trocar within the tubular sleeve 10 the deflected grip section 20 of handle 18 engages almost fittingly in the longitudinal slot 58 of the second handle 50. When this is done, the rotational position of the handles 16, 50 is fixed relative to each other or in front of the grip 50 and the tissue protection sleeve 10.

Figure 3:
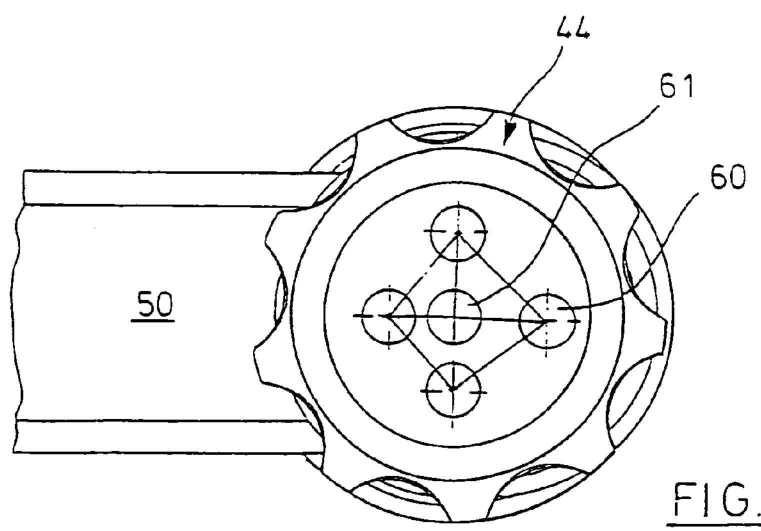
FIG. 3 is an end view of the trocar of the device according to FIGS. 1 and 2.

As can be seen especially in FIG. 3, the shaft of trocar 30 has five axially parallel bore holes 60, which extend from the proximal end to the end section 32 of trocar 30 and are intended to receive a guide wire (not shown) for drilling bone. As can be seen in FIG. 1, in the solid part of the shaft of trocar 30 a central bore 61 is provided, whilst the other bores between the flanges 36, 38 and the stopper-shaped end 32 are configured as axially parallel grooves, as shown at 62 in FIG. 1. Of course, grooves 62 could be formed as bores within a solid part of the trocar shaft.

The rotational position of the trocar 30 within the tissue protection sleeve 10 can be adjusted by the surgeon by rotating the knob 44. By gripping both handles 16, 50 manually, the rotational position of trocar 30 can be fixed, in that the annular section 48 cants into the annular recess 46 and consequently securely clamps trocar 30. As can be seen, handle 50 is shorter than handle 16. In this fashion, holding tissue protection sleeve 10 is possible without actuating or grasping handle 50.

If during the surgical procedure it is found that the guide wire introduced into the central bore hole 61, upon X-ray inspection, has not achieved the desired position, a second guide wire is introduced into one of the bore holes 60 after turning the trocar 30. If the second guide wire has assumed the correct position, the first guide wire is removed. After complete introduction of the guide wire, the trocar is removed from the tissue protection sleeve 10 and, with the aid of a drilling tool threaded onto the guide wire, the bone can be drilled. Note, as shown in FIG. 3, the bore holes 60 can be non-symmetrically oriented around central bore hole 61 to allow more positional orientations.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for installation of a guide wire for a drilling tool in a correct positional arrangement in a bone comprising:

a tissue protection sleeve having a longitudinal axis, which has at one end a handle projecting laterally with respect to the sleeve longitudinal axis and a trocar having a longitudinal axis, said trocar for introduction into the tissue protection sleeve from the handle end for rotatable movement within said sleeve, whereby the trocar is rotatable in the tissue protection sleeve and has a central bore hole and a plurality of axially parallel bore holes surrounding said central bore, through which holes, a guide wire can be passed, said trocar having a handle unconnected to the sleeve handle extending laterally to the trocar longitudinal axis which can be oriented by rotation about the sleeve longitudinal axis in an approximately parallel direction to the sleeve handle, said trocar handle having one end which engages an end of the trocar situated outside of the tissue protection sleeve, so that the normally freely rotatable trocar is fixed in the direction of rotation relative to the tissue protection sleeve when both handles are manually clamped against each other by deflecting at least one of the handles the trocar having a shaft extending along the longitudinal axis with a knob and a flange mounted thereon on opposite sides of the trocar handle, the trocar handle having an annular portion for rotatably receiving the shaft intermediate the knob and the flange, the annular portion of the trocar handle is rotatable, axially moveable and tiltable with respect to the trocar shaft longitudinal axis.

2. The device as set forth in claim 1 wherein the trocar has an annular recess in which an annular engagement section of the second handle engages, so that the annular engagement section cants into said annular recess and clampingly engages the trocar when the handles are clamped against each other.

3. The device as set forth in claim 2 wherein a section of the trocar is configured as a rotary knob at the end facing away from the tissue protection sleeve.

4. The device as set forth in claim 1 wherein a shaft of the trocar has a plurality of radial flanges arranged at axial intervals, external diameters of said flanges are somewhat smaller than the internal diameter of the tissue protection sleeve and a part of the axially parallel bore holes continues along sections of the shaft as axially parallel grooves between the flanges, which shaft sections are formed having smaller diameters then said flanges.

5. The device as set forth in claim 1 wherein the trocar handle is comprised of elastically deflectable material.

6. The device as set forth in claim 1 wherein the trocar handle is arranged above the sleeve handle.

7. The device as set forth in claim 6 wherein the trocar handle has a longitudinal slot in a section facing towards the sleeve handle such that a section of the sleeve handle engages in the longitudinal slot.

8. The device as set forth in claim 1 wherein at least two of the bore holes surrounding the central bore are at different radii with respect to a central longitudinal axis of said trocar.

9. A device for the installation of a guide wire for a drilling tool in a correct positional arrangement in a bone comprising:

a tubular sleeve having a handle at a first end and an internal bore extending along an axis; and a trocar having a bore hole for receiving the guide wire, said trocar sized for insertion into the internal bore of said tubular sleeve and for rotation therein, said trocar having a handle unconnected to the sleeve handle, said handles extending generally in parallel immediately prior to their engagement at a first end and at least one bore therethrough, said trocar handle having a shaft including a recess for engaging a shaft of said sleeve handle upon rotation of said trocar handle about the axis of the sleeve bore into general parallel alignment with said sleeve handle the trocar having a shaft extending along the longitudinal axis with a knob and a flange mounted thereon on opposite sides of the trocar handle, the trocar handle having an annular portion for rotatably receiving the trocar shaft intermediate the knob and the flange, the annular portion of the trocar handle is rotatable, axially moveable and tiltable with respect to a longitudinal axis of the trocar shaft.

10. The device as set forth in claim 9 wherein said trocar handle is deflectable for moving said slot into engagement with said cylindrical portion of said sleeve handle.

11. The device as set forth in claim 10 wherein said trocar handle at said first trocar end is spaced along a longitudinal axis of said trocar and said sleeve after assembly, beyond said sleeve handle at said first sleeve end.

12. The device as set forth in claim 11 wherein said trocar handle is made of an elastically deformable material.

13. The device as set forth in claim 12 wherein the trocar handle is made of plastic.

14. The device as set forth in claim 9 wherein said trocar has a central bore and a plurality of parallel bores around said central bore, at least two of said plurality of bores are at a different radii with respect to a central longitudinal axis of said central bore.

15. The device as set forth in claim 14 wherein a shaft of the trocar has a plurality of radial flanges arranged at axial intervals, external diameters of said flanges are somewhat smaller than the internal diameter of the tissue protection sleeve and a part of the parallel bore holes continues along sections of the shaft as axially parallel grooves between the flanges, which shaft sections are formed having smaller diameters than said flanges.

16. A device for the installation of a guide wire for a drilling tool in a correct positional arrangement in a bone comprising:

a trocar having a shaft with a plurality of bores therethrough and a handle portion at a first end thereof; and a sleeve having a bore extending along an axis for rotatably receiving said trocar shaft, said sleeve having a handle portion mounted at a first end thereof unconnected to the trocar handle, said trocar handle rotatable about the sleeve bore axis and having a recess for receiving a part of said sleeve handle portion when said trocar shaft is received within said bore of said sleeve wherein said sleeve handle has a cylindrical shaft portion and said trocar handle shaft is bent and said recess in said trocar handle is a slot with said slot moveable into engagement with said cylindrical shaft portion, the sleeve and trocar handles extending generally in parallel immediately prior to the engagement of the slot and shaft the trocar having a shaft extending along the longitudinal axis with a knob and a flange mounted thereon on opposite sides of the trocar handle, the trocar handle having an annular portion for rotatably receiving the trocar shaft intermediate the knob and the flange, the annular portion of the trocar handle is rotatable, axially moveable and tiltable with respect to a longitudinal axis of the trocar shaft.

17. A device for the installation of a guide wire for a drilling tool in a correct positional arrangement in a bone comprising:

a tubular sleeve having a longitudinal axis and a handle extending transversely to the longitudinal sleeve axis at a first end and an internal bore; and a trocar having a longitudinal axis and a bore hole for receiving the guide wire, said trocar sized for insertion into the internal bore of said tubular sleeve and for rotation therein, said trocar having a handle unconnected to the sleeve handle extending transverse to said trocar longitudinal axis at a first end and at least one bore therethrough, said trocar handle having a shaft including a recess for engaging a deflectable shaft of said sleeve handle upon rotation of said trocar handle with respect to the sleeve longitudinal axis into alignment with said sleeve handle the trocar having a shaft extending along the longitudinal axis with a knob and a flange mounted thereon on opposite sides of the trocar handle, the trocar handle having an annular portion for rotatably receiving the trocar shaft intermediate the knob and the flange, the annular portion of the trocar handle is rotatable, axially moveable and tiltable with respect to the trocar shaft longitudinal axis.

18. The device as set forth in claim 17 wherein said deflectable sleeve handle has a cylindrical shaft portion and said trocar handle shaft is bent and said recess in said trocar handle is a slot with said slot moveable into engagement with said cylindrical shaft portion.

* * * * *